(12) United States Patent
Bodmer et al.

(10) Patent No.: US 6,183,452 B1
(45) Date of Patent: Feb. 6, 2001

(54) ASEPTIC PROTECTOR FOR SKIN PENETRATING DEVICES

(76) Inventors: E. James Bodmer, 2135 E. Calle Maderas, Mesa, AZ (US) 85213; Antonius Su, 457 W. Mendoza Cir., Mesa, AZ (US) 85210

(*) Notice: Under 35 U.S.C. 154(b), the term of this patent shall be extended for 0 days.

(21) Appl. No.: 09/212,840

(22) Filed: Dec. 16, 1998

(51) Int. Cl.[7] ..................................................... A61F 13/00
(52) U.S. Cl. ............................ 604/308; 602/11; 602/22; 602/30
(58) Field of Search ..................................... 604/289, 290, 604/293, 263, 292, 304, 308; 606/53, 54, 59; 602/22, 30–31, 901

(56) References Cited

U.S. PATENT DOCUMENTS

| | | | |
|---|---|---|---|
| 2,069,643 | * | 2/1937 | Burke .................................. 128/165 |
| 4,089,066 | * | 5/1978 | Dethman . |
| 4,940,046 | * | 7/1990 | Jacoby . |
| 5,181,914 | * | 1/1993 | Zook ................................... 604/307 |

* cited by examiner

Primary Examiner—Glenn K. Dawson
Assistant Examiner—Catherine Serke
(74) Attorney, Agent, or Firm—John D. Lister

(57) ABSTRACT

An aseptic protector for skin penetrating devices includes a body of deformable material for accepting and encapsulating a protruding portion of a skin penetrating device, such as a pin or drain, from a location where the skin penetrating device protrudes from a skin surface to a location spaced outwardly from the skin surface. The body of deformable material functions as a buffer and inhibits movement of the skin penetrating device. The body of deformable material includes an aseptic agent, preferably dispersed throughout the body of material, for contacting the skin surface and the skin penetrating device at the location where the skin penetrating device penetrates the skin surface to prevent, inhibit or arrest infection where the skin penetrating device penetrates the skin surface. Preferably, the body of deformable material is encased within a tubular casing which may be provided with a skirt of flexible material to form an aseptic veil that surrounds the location where the skin penetrating device penetrates the skin surface.

16 Claims, 2 Drawing Sheets

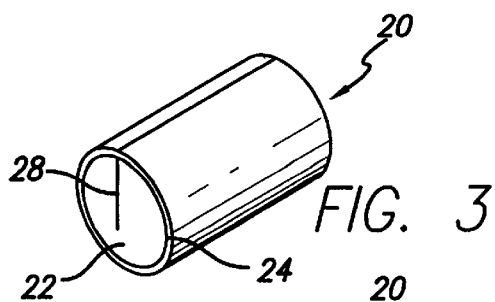
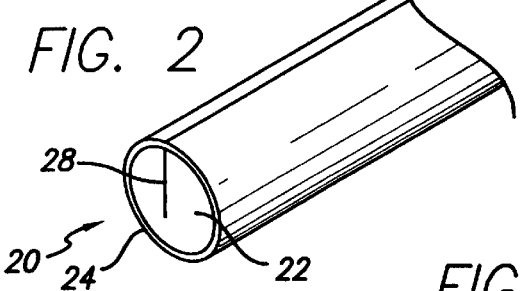
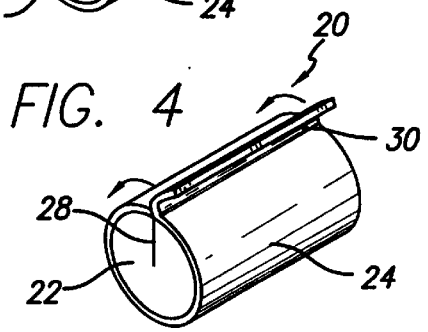
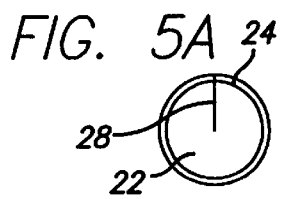
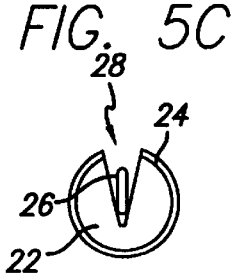
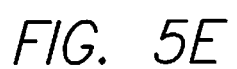
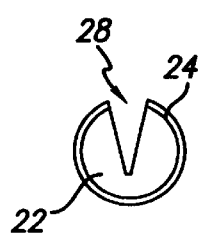
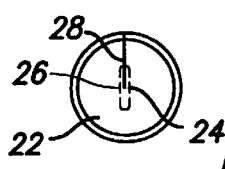
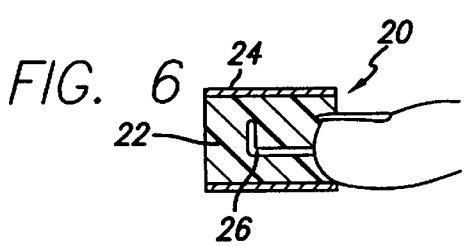
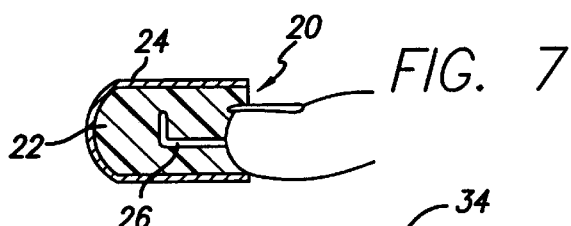
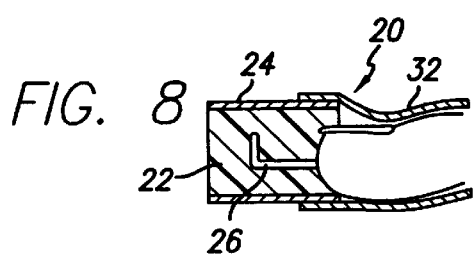
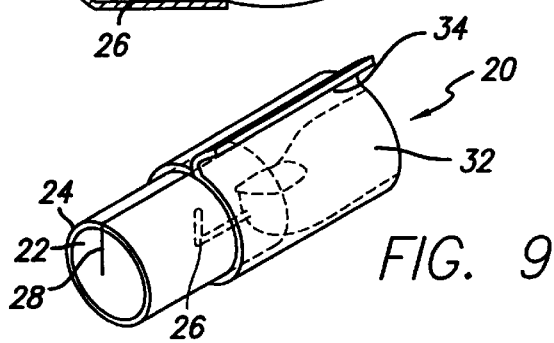

ASEPTIC PROTECTOR FOR SKIN PENETRATING DEVICES

BACKGROUND OF THE INVENTION

The present invention relates to an aseptic protector and, in particular, to an aseptic protector for use with skin penetrating devices that functions: to prevent, inhibit or arrest infection where the skin penetrating device penetrates a patient's skin; as a buffer to prevent injury to a patient or clinician or damage to the skin penetrating device; and to inhibit unwanted movement of the skin penetrating device once it is in place.

Frequently, medical procedures commonly used in plastic, general, orthopedic and oral surgery involve the use of skin penetrating devices, such as but not limited to, pins to maintain bones or sections of fractured bones in a fixed relationship and proper alignment with respect to each other; intravenous lines; plastic drain tubes for draining fluids from within the body after a medical procedure has been performed; and other similar devices. In many instances these skin penetrating devices may have to remain in place for long periods of time, e.g. about three to six weeks in certain orthopedic procedures, and circumstances may prevent washing the skin in the general area of the skin penetrating device. The points of skin penetration by these devices are potential locations where infectious processes can commence and spread into the body. Thus, there has long been a need to provide a sterile, aseptic environment about these skin penetrating devices where the devices pass though the skin of the patient.

Another problem encountered in the use of these skin penetrating devices is the need to keep these devices from being inadvertently damaged and/or moved by external forces, e.g. when a patient or a clinician inadvertently brushes the protruding portion of the skin penetrating device against or rapidly brings the protruding portion of the skin penetrating device into contact with something hard or catches the device on a piece of clothing or other more rigid obstruction. The types of inadvertent movements to be prevented or inhibited include lateral, twisting and rotational movements of the devices as well as movement of the devices further into or out from the body. In addition to the need to keep the devices from being inadvertently moved or damaged, certain of the skin penetrating devices, e.g. the pins used in orthopedic procedures, have sharp or pointed ends which, if contacted, can inflict injury upon the patient or a clinician.

As shown in FIG. 1, current practices which include the use of end caps on pins, do not provide an aseptic environment about the skin penetrating device nor do they function effectively as a buffer to protect the patient or clinician or to prevent movement of or damage to the pin. Thus, not only has there been a need to provide a sterile, aseptic environment about these skin penetrating devices where the devices pass though the skin of the patient, there also has been a need to buffer the skin penetrating devices against inadvertent movement and damage and patients and clinicians against accidental injury from the skin penetrating devices.

SUMMARY OF THE INVENTION

An aseptic protector of the present invention for skin penetrating devices includes a body of deformable material for accepting and encapsulating a protruding portion of a skin penetrating device, such as a pin or drain, from a location where the skin penetrating device protrudes from a skin surface to a location spaced outwardly from the skin surface. The body of deformable material functions as a buffer to protect the patient and clinicians from being injured on a skin penetrating device, such as a pin projecting from the patient and to protect the skin penetrating device from damage; and inhibits movement of the skin penetrating device.

In one embodiment of the invention, the body of deformable material has a longitudinally extending slit that permits the body of deformable material to be opened to receive a skin penetrating device and then closed to encapsulate all (such as when used with a pin) or a portion (such as when used with a drain) of the skin penetrating device protruding from the skin surface. In certain other embodiments, the body of deformable material is formed from a material or materials that cure(s), react(s) or solidifies to become a deformable plastic material or deformable resilient material after the aseptic protector has been applied to the skin penetrating device.

The body of deformable material includes an aseptic agent, preferably dispersed throughout the body of material, for contacting the skin surface and the skin penetrating device at the location where the skin penetrating device penetrates the skin surface to prevent, inhibit or arrest infection where the skin penetrating device penetrates the skin surface.

Preferably, the body of deformable material is encased within a tubular casing which may be provided with a skirt of flexible material to form an aseptic veil that surrounds the location where the skin penetrating device penetrates the skin surface. Where the body of deformable material is provided with a longitudinally extending slit, the tubular casing and skirt (if used) are also provided with a slit aligned with the slit in the body of deformable material and, preferably, provided with a means, such as but not limited to, an adhesively coated tab to close and seal the slit.

BRIEF DESCRIPTION OF THE DRAWINGS

FIG. 1 shows toe with a pin that has a cap on the end of the pin in accordance with current practices.

FIG. 2 is a schematic perspective view of a portion of first aseptic protector of the present invention that is sized in length to enable the protector to be cut into a plurality of sections of desired lengths.

FIG. 3 is a schematic perspective view of a second aseptic protector of the present invention precut and sized to a desired length.

FIG. 4 is a schematic perspective view of a third aseptic protector of the present invention with a sealing tab.

FIG. 5 is a schematic representation showing the aseptic protector of the present invention being opened and then closed about a skin penetrating device to encase the device.

FIG. 6 is a schematic longitudinal section through an aseptic protector of the present invention, with a casing that is open at both ends, applied to the toe of a patient with a pin encased within the protector.

FIG. 7 is a schematic longitudinal section through an aseptic protector of the present invention, with a casing that is closed at one end, applied to the toe of a patient with a pin encased within the protector.

FIG. 8 is a schematic longitudinal section through an aseptic protector of the present invention, including casing and a skirt at one end, applied to the toe of a patient with a pin encased within the protector.

FIG. 9 is a schematic perspective view of an aseptic protector of the present invention, including a casing and a skirt at one end with a sealing tab, applied to the toe of a patient with a pin encased within the protector.

DESCRIPTION OF THE PREFERRED EMBODIMENTS

Figure 10:
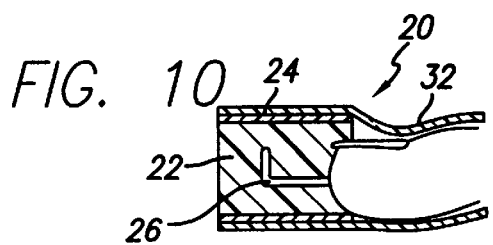
FIG. 10 is a schematic longitudinal section through an aseptic protector of the present invention, including a casing covered by a sleeve that forms a skirt at one end of the protector, applied to the toe of a patient with a pin encased within the protector.

The aseptic protector 20 of the present invention for skin penetrating devices includes a body 22 of deformable material for accepting and encapsulating a protruding portion of a skin penetrating device 26, such as a pin or drain, from a location where the skin penetrating device protrudes from a skin surface to a location spaced outwardly from the skin surface. Preferably, the aseptic protector 20 also includes an outer casing 24.

The aseptic protector 20 can be provided, as shown in FIG. 2, in extended lengths adapted to be cut and sized to desired lengths for particular applications or, as shown in FIG. 3, in pre-cut or pre-formed lengths already sized for a particular application. The length of the aseptic protector 20 will vary according to the length of the skin penetrating device projecting from the surface of the skin and/or the type of application. For example, for encasing pins and the like, the length of the aseptic protector 20 is longer than the length of the portion of the skin penetrating device 26 projecting from the surface of the skin. For intravenous lines, drains and the like, the length of the aseptic protector 20 will be sufficient, typically about 0.25 inches to about 1.5 inches and preferably, about 0.5 inches to about 1.0 inches to provide the desired buffering and stabilizing function required for the application.

The transverse dimensions (diameter in the preferred forms of the invention) of the aseptic protector 20 perpendicular to the longitudinal centerline of the aseptic protector are greater than the corresponding transverse dimensions of the skin penetrating device 26, especially at the end of aseptic protector 20 placed against the skin surface, to provide an aseptic environment around the point of entry of the skin penetrating device into the skin of the patient, to provide stability to prevent unwanted movement of the skin penetrating device, and to function as a buffer for the skin penetrating device, the patient and clinicians. The transverse dimensions of the skin penetrating devices 26, where the skin penetrating devices penetrate the skin of the patient, typically range from about 0.25 inches to about 0.50 inches for pins and similar devices and from about 0.5 inches to about 1.0 inches or greater for intravenous lines, drains and similar devices. The transverse dimensions of the aseptic protector 20 range from about 0.25 inches to about 2.0 inches greater than the corresponding transverse dimensions of the skin penetrating device and preferably, from about 0.5 inches to about 1.5 inches greater than the corresponding dimensions of the skin penetrating devices, especially at the end of the aseptic protector to be place against the surface of the skin. Where the aseptic protector 20 is not about 0.25 inches or greater in transverse dimensions than the corresponding transverse dimensions of the skin penetrating device 26 (where the skin penetrating device penetrates the skin), the aseptic environment surrounding the point of entry of the skin penetrating device may not be large enough to provide adequate protection against infection in certain applications and the aseptic protector 20 may not provide the stability and buffering function desired or required. Thus, increasing the transverse dimensions of the aseptic protector up to a certain point has a beneficial effect. However, as the difference in the relative transverse dimensions of the skin penetrating device 26 and the aseptic protector 20 become increasingly greater the benefits of increasing the size of the aseptic environment about the point penetration and the stability and buffering function provided by the aseptic protector 20 gradually decrease. Thus, transverse dimensions of the aseptic protector 20 greater than about 2.0 inches than the corresponding dimensions of the skin penetrating device, where the skin penetrating device penetrates the skin, would not particularly enhance the performance of the aseptic protector and such greater sizes could, in certain applications, become a hinderance. While the aseptic protector 20, preferably, is cylindrical in shape, the aseptic protector 20 can have a truncated cone shape for certain applications and the transverse cross section of the aseptic protector 20 can be other than round, such as but not limited to, oval, square, rectangular or triangular.

When applied to a protruding portion of a skin penetrating device 26, the body 22 of deformable material may be in various physical states as illustrated by the following examples. The body 22 of deformable material may be a deformable plastic material that remains a deformable plastic material and, when applied to a skin penetrating device, conforms to the exterior surface of the skin penetrating device and the skin surface in the area where the skin penetrating device penetrates the skin. The body 22 of deformable material may be a body of a deformable resilient material that remains a body of deformable resilient material and, when applied to a skin penetrating device, conforms to the exterior surface of a protruding portion of the skin penetrating device and the skin surface in the area where the skin penetrating device penetrates the skin, such as but not limited to a silicone rubber-like material. As used herein, the term "deformable plastic material" means a deformable material capable of being molded, shaped, formed or modeled into a desired shape and capable of conforming to or being conformed to a surface, such as the exterior surface of a protruding portion of skin penetrating device and "deformable resilient material" means a deformable material capable of recovering its size and shape after deformation and, preferably, of conforming to or being conformed to a surface, such as the exterior surface of a protruding portion of skin penetrating device. The body 22 of deformable material may initially consist of two fluids (e.g. a polymer and a catalyst) which, when combined, form a body of deformable plastic material and preferably, a body of deformable resilient material about the protruding portion of a skin penetrating device that conforms to the exterior surface of the skin penetrating device and the skin surface in the area where the skin penetrating device penetrates the skin, such as but not limited to a silicone rubber-like material. The body 22 of deformable material may initially be a soft deformable plastic material, e.g. having a consistency like or similar to that of a thick paste or dough, that when applied to a skin penetrating device conforms to the exterior surface of a protruding portion of a skin penetrating device and the skin surface in the area where the skin penetrating device penetrates the skin and, preferably, cures (e.g. air cures) after application to a protruding portion of a skin penetrating device to form a body of firmer deformable plastic material or, preferably, a body of deformable resilient material about the protruding portion of a skin penetrating device. The body of deformable material may initially be a soft deformable plastic material, e.g. having a consistency like or similar to that of a thick paste or dough, that when applied to a skin penetrating device conforms to the exterior surface of a protruding portion of a skin penetrating device and the skin surface in the area where the skin penetrating device penetrates the skin and, preferably, through combination with a catalyst reacts to form a body of firmer deformable plastic material or, preferably, a body of deformable resilient material about a protruding portion of the skin penetrating device, e.g. like or similar to a moldable foot composition sold by Pedinol Corporation under the trademark "PEDIPLAST".

Thus, in its preferred forms the body of deformable material: can be molded, formed about or conforms or substantially conforms to the exterior surface of a protruding portion of the skin penetrating device to encapsulate a protruding portion of the skin penetrating device; conforms or substantially conforms, when applied, to the contour of the surface of the skin in the area about the point or location where the skin penetrating device penetrates the skin; absorbs external shocks that would otherwise be transmitted directly to the protruding portion of the skin penetrating device; provides stability and helps to prevent or limit movement (lateral or rotational movement) of the projecting portion of the skin penetrating device; and protects the patient and clinicians from inadvertently injuring themselves on a projecting portion of the skin penetrating device.

Where a catalytic or curing reaction is involved, such as in two of the examples given above, the temperature of any exothermic reaction must be less than the temperature at which the aseptic agent in the material would be made ineffective. In addition, the body of deformable material is sterile and not caustic or otherwise detrimental to the skin layers. While the deformable material may remain or cure into a deformable plastic state, as discussed above, preferably, the body 22 of deformable material is or becomes a deformable resilient material for gripping the skin penetrating device and better absorbing external shocks. It is also preferred that the body of deformable material be capable of being readily cut with a sharp instrument after its application to facilitate the eventual removal of the aseptic protector from a skin penetrating device, especially for embodiments of the invention wherein there is no preformed slit in the body of deformable material.

The body 22 of deformable material has an aseptic agent or means, at least at the end of the body of deformable material intended to be placed in contact with the skin surface 38 of the patient, e.g. a coating, and preferably, dispersed throughout the body of deformable material for preventing, inhibiting or arresting infection where the skin penetrating device penetrates the skin. For example, the aseptic agent may be an antibiotic for destroying pathogenic microorganisms.

As stated above, preferably, the aseptic protector 20 of the present invention has a tubular casing 24 encasing the body 22 of deformable material. Preferably, the casing is made of a polymeric material, such as but not limited to polypropylene, and though flexible, the casing typically is more rigid than the body 22 of deformable material. While not preferred, the casing can also be made of a flexible cloth or sheet material, such as but not limited to a thin polymeric film e.g. a polypropylene film. In certain embodiments of the invention, the tubular casing 24 is air permeable to facilitate the cure or reaction of the materials forming of the body 22 of deformable material when such material(s) are used.

Turning now to more specific embodiments of the invention, FIG. 2–4 show embodiments of the aseptic protector 20 wherein the body 22 of deformable material and the tubular casing 24 are provided with a longitudinally extending slit 28. Although the slit 28 can be made in the aseptic protector by the clinician immediately prior to application of the protector, preferably, the slit is formed in the body 22 of deformable material when the aseptic protector in manufactured. Preferably, the slit 28 extends for the entire length of the aseptic protector 20 and passes from the exterior surface of the aseptic protector through and beyond the center of the aseptic protector to facilitate (as sequentially shown in FIG. 5) opening the aseptic protector, inserting a protruding portion of a skin penetrating device 26 within the aseptic protector, and closing the aseptic protector about the protruding portion of the skin penetrating device 26 to encase or encapsulate the protruding portion of the skin penetrating device 26 within the aseptic protector. As shown in the last figure of FIG. 5, once the aseptic protector 20 is closed about the protruding portion of the skin penetrating device 26, the aseptic protector can be maintained in the closed position by applying or wrapping adhesive tape 42 about the exterior surface of the aseptic protector or otherwise securing the aseptic protector in a closed position. If an aseptic protector 20 is used, such as the aseptic protector of FIG. 4, which has its own sealing tab 30 that overlaps the slit 28 and adheres to the exterior surface of the aseptic protector on the opposite side of the slit 28, the use of adhesive tape to keep the aseptic protector closed is not required. If desired a pressure sensitive adhesive can be used on the sealing tab 30 or a release strip (not shown) can be applied to the adhesive coated surface of the sealing tab that is removed immediately prior to sealing the aseptic protector about the skin penetrating device 26.

FIG. 6 shows an aseptic protector 20, applied to the protruding portion of a skin penetrating device 26, such as a pin or the like, which has a casing 24 and is open at both ends. The end of the body 22 of deformable material in contact with the skin of the patient conforms or substantially conforms to the contours of the patient's skin. The aseptic protector of FIG. 6 may have a body of deformable material and a casing with slit such as the slit shown in FIG. 3 or, if the body 22 of deformable material is formed from a material or materials that react(s), cure(s) or solidifies to become a deformable plastic material or deformable resilient material after application to the skin penetrating device 26, the body 22 of deformable material and the casing 24 may not have a slit therein with the protruding portion of the skin penetrating device 26 being inserted into the aseptic protector rather than opening up the aseptic protector as shown in FIG. 5. Depending on the initial viscosity of such reacting, curing or solidifying materials, means, such as but not limited to tape, may have to be applied to the open end of the casing 24 while the material(s) cure, react or solidify into the deformable material. In this and other embodiments of the invention using reacting, curing or solidifying materials to form the body of deformable material at the time of application, the casing 24 may be filled with the materials prior to inserting the projecting portion of the skin penetrating device into the casing or the body of deformable material may be formed in situ about the skin penetrating device after it has been inserted into the casing 24 of the aseptic protector.

FIG. 7 shows an aseptic protector 20, applied to the protruding portion of a skin penetrating device 26, such as a pin or the like, which has a casing 24 that is closed at one end. The end of the body 22 of deformable material in contact with the skin of the patient conforms or substantially conforms to the contours of the patient's skin. The aseptic protector of FIG. 7 may have a body of deformable material and a casing with a slit such as the slit shown in FIG. 3 or, if the body 22 of deformable material is formed from a material or materials that react(s), cure(s) or solidifies to become a deformable plastic material or deformable resilient material after application to the skin penetrating device 26, the body 22 of deformable material and the casing 24 may not have a slit therein. For example, in this and other embodiments of the invention with no slit in the deformable material and casing, the material or materials which cure, react or solidify to form the deformable plastic material or deformable resilient material can be injected into the casing 24, e.g. from a syringe. The casing 24, filled with the material(s), can then be applied to the protruding portion of the skin penetrating device by inserting the protruding portion of the skin penetrating device 26 into the aseptic protector rather than opening up the aseptic protector as shown in FIG. 5.

FIG. 8 shows an aseptic protector 20, applied to the protruding portion of a skin penetrating device 26, such as a pin or the like, which has a casing that is open at both ends and a skirt 32 that forms a protective veil about the skin penetrating device 26. Preferably, the skirt 32, used in this embodiment of the invention and the other embodiments discussed below, is made of a flexible, pliable, elastic material, such as but not limited to 10—10 barrier drape, marketed by Medical Concepts Development Inc. of St. Paul, Minn., that can conform or substantially conform to the skin of the patient to further isolate the point of entry of the skin penetrating device 26 from external conditions. The skirt 32 may be treated with an aseptic agent. The end of the body 22 of deformable material and the portions of the skirt 32 in contact with the skin of the patient conform or substantially conform to the contours of the patient's skin. The aseptic protector of FIG. 8 may have a body of deformable material and a casing with a slit such as the slit shown in FIG. 9 or, if the body 22 of deformable material is formed from a material or materials that react(s), cure(s) or solidifies to become a deformable plastic material or deformable resilient material after application to the skin penetrating device 26, the body 22 of deformable material and the casing 24 may not have a slit therein with the protruding portion of the skin penetrating device 26 being inserted into the aseptic protector rather than opening up the aseptic protector as shown in FIG. 5. Depending on the initial viscosity of such reacting, curing or solidifying materials, means, such as but not limited to tape, may have to be applied to the open end of the casing 24 while the material(s) cure, react or solidify into the deformable material. In the embodiment of FIG. 9, the skirt 32 is provided with a sealing tab 34, such as sealing tab 30, to seal the veil formed about the entry point by the skirt.

Figure 11:
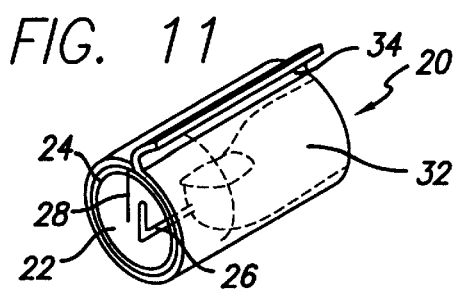
FIG. 11 is a schematic perspective view of an aseptic protector of the present invention, including a casing covered by a sleeve with a sealing tab that forms skirt at one end of the protector, applied to the toe of a patient with a pin encased within the protector.

FIG. 10 shows an aseptic protector 20, applied to the protruding portion of a skin penetrating device 26, such as a pin or the like, which has a casing that is open at both ends and a skirt 32 that extends for the entire length or substantially the entire length of the casing and forms a protective veil about the skin penetrating device 26. The skirt 32 may be treated with an aseptic agent. The end of the body 22 of deformable material and the portions of the skirt 32 in contact with the skin of the patient conform or substantially conform to the contours of the patient's skin. The aseptic protector of FIG. 10 may have a body of deformable material and casing with slit such as the slit shown in FIG. 11 or, if the body 22 of deformable material is formed from a material or materials that react(s), cure(s) or solidifies to become a deformable plastic material or deformable resilient material after application to the skin penetrating device 26, the body 22 of deformable material and the casing 24 may not have a slit therein with the protruding portion of the skin penetrating device 26 being inserted into the aseptic protector rather than opening up the aseptic protector as shown in FIG. 5. Depending on the initial viscosity of such reacting, curing or solidifying materials, means, such as but not limited to tape, may have to be applied to the open end of the casing 24 while the material(s) cure, react or solidify into the deformable material. In the embodiment of FIG. 11, the skirt 32 is provided with a sealing tab 34, such as sealing tab 30, to seal the casing 24 as well as the veil formed about the entry point by the skirt.

Figure 12:
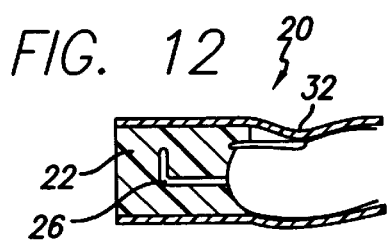
FIG. 12 is a schematic longitudinal section through an aseptic protector of the present invention, including a sleeve that forms both a casing for the protector and a skirt at one end of the protector, applied to the toe of a patient with a pin encased within the protector.

FIG. 12 shows an aseptic protector 20, applied to the protruding portion of a skin penetrating device 26, such as a pin or the like, which has a casing and skirt 32 that extends for the length of the body 22 of deformable material and forms a protective veil about the skin penetrating device 26. This embodiment of the aseptic protector 20 has no separate casing 24. The skirt 32 may be treated with an aseptic agent. The end of the body 22 of deformable material and the portions of the skirt 32 in contact with the skin of the patient conform or substantially conform to the contours of the patient's skin. The aseptic protector of FIG. 12 may have a body of deformable material with a slit or, if the body 22 of deformable material is formed from a material or materials that react(s), cure(s) or solidifies to become a deformable plastic material or deformable resilient material after application to the skin penetrating device 26, the body 22 of deformable material and the casing 32 may not have a slit therein with the protruding portion of the skin penetrating device 26 being inserted into the aseptic protector rather than opening up the aseptic protector as shown in FIG. 5. Depending on the initial viscosity of such reacting, curing or solidifying materials, means, such as but not limited to tape, may have to be applied to the open end of the casing 24 while the material(s) cure, react or solidify into the deformable material. If the embodiment of FIG. 12 has a slit, the skirt 32 is provided with a sealing tab 34, such as sealing tab 30, to seal the slit formed in the body of deformable material 22 as well as the veil formed about the entry point by the skirt.

Figure 13:
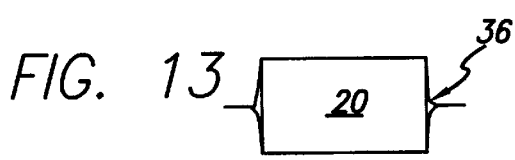
FIG. 13 is schematic side view of an aseptic protector of the present invention vacuum packaged in a plastic film.

FIG. 13 shows the aseptic protector 20 of the present invention vacuum packaged in a clear, air impermeable polymeric film package 36 or the like. This type of packaging not only maintains the aseptic protector 20 in a sterile environment prior to use, but where an air curable material is used for the body 22 of deformable material, the vacuum packaging prevents the body 22 of deformable material from curing prematurely (prior to application to the skin penetrating device 26).

Figure 14:
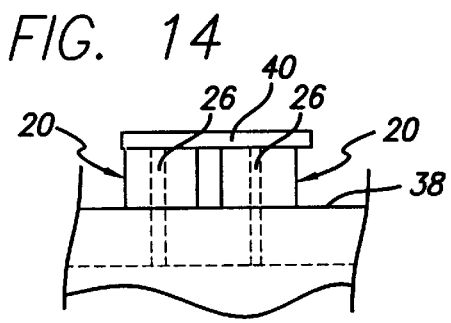
FIG. 14 is a schematic side view showing aseptic protectors applied to pins intermediate a medical appliance and the skin surface of the patient.

FIG. 14 shows two aseptic protectors 20 of the present invention encapsulating or encasing projecting portions of skin penetrating devices 26, pins, and interposed between the skin surface 38 of a patient and an appliance 40 spaced outwardly from the skin surface of the patient. The aseptic protectors in this instance also function as spacers between to skin surface 38 and the appliance 40 to help maintain the appliance in the desired position.

Figure 15:
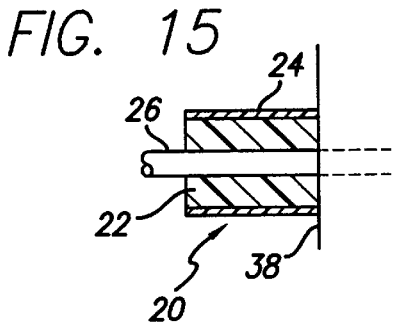
FIG. 15 is a schematic longitudinal section through an aseptic protector of the present invention applied to a drain, an intravenous line, or a similar skin penetrating device.

FIG. 15 shows an aseptic protector 20, applied to a protruding portion of a skin penetrating device 26, such as a drain, an intravenous line or the like. The aseptic protector has a casing 24 and is open at both ends. The end of the body 22 of deformable material in contact with the skin of the patient conforms or substantially conforms to the contours of the patient's skin. The aseptic protector of FIG. 15 may have a body of deformable material and a slit such as the slit shown in FIG. 3 or, if the body 22 of deformable material is formed from a material or materials that react(s), cure(s) or solidifies to become a deformable plastic material or deformable resilient material after application to the skin penetrating device 26, the body 22 of deformable material and the casing 24 may not have a slit therein with the protruding portion of the skin penetrating device 26 being inserted through the aseptic protector and the body of deformable material being formed in situ about the skin penetrating device rather than opening up the aseptic protector as shown in FIG. 5. Depending on the initial viscosity of such reacting, curing or solidifying materials, means, such as but not limited to tape, may have to be applied to the open end of the casing 24 while the material(s) cure, react or solidify into the deformable material.

Figure 16:
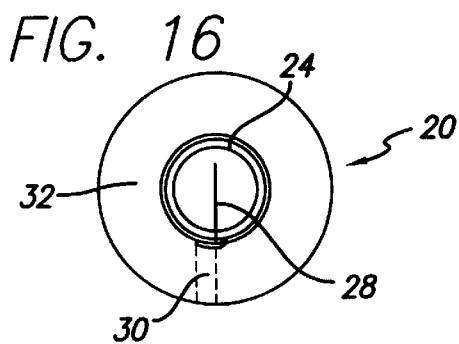
FIG. 16 is a top schematic view of an aseptic protector of the present invention provided with a skirt that flares out from one end of the protector.
Figure 17:
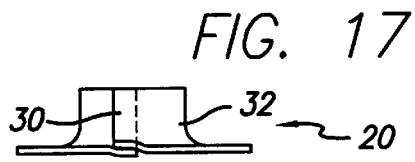
FIG. 17 is a side schematic view of an aseptic protector of FIG. 16.
Figure 18:
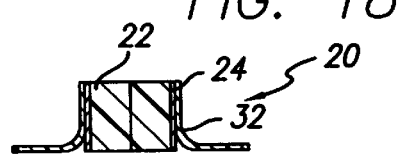
FIG. 18 is a schematic longitudinal section of an aseptic protector of FIG. 16.
Figure 19:
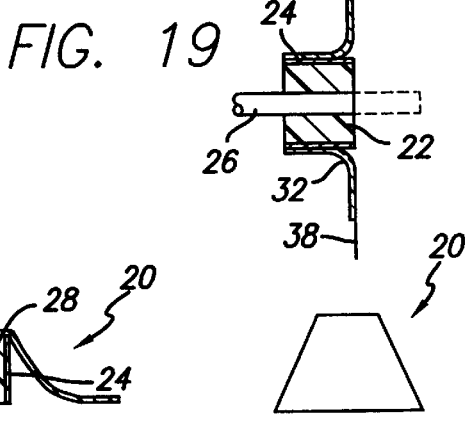
FIG. 19 is a schematic longitudinal section of an aseptic protector of FIG. 16 applied to a drain, intravenous line, or similar skin penetrating device.

FIGS. 16–17 show an aseptic protector especially suited for use with drains, intravenous lines and the like, similar to the aseptic protector of FIG. 15, but provided with a skirt 32 secured to exterior side surface of the casing 24. The skirt 32 flares outward from the end of the body 22 of deformable material intended to contact the patient's skin 38 to better form, as shown in FIG. 19, a veil about the point of skin penetration by a skin penetrating device 26.

Figure 20:
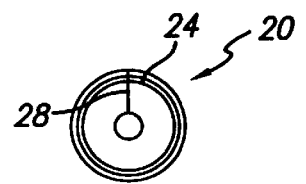
FIG. 20 is an end view of an aseptic protector of the present invention which has a longitudinally extending orifice therein for receiving a pin, drain, intravenous line, or similar skin penetrating device.
Figure 21:
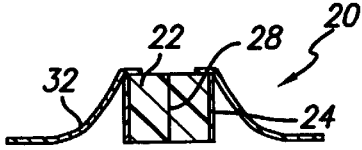
FIG. 21 is a schematic longitudinal section of an aseptic protector which, except for the attachment of the skirt to the body of the protector, is similar to the aseptic protector of FIG. 16.
Figure 22:
FIG. 22 is a schematic side elevation of truncated cone shaped aseptic protector of the present invention.

FIG. 20 shows an aseptic protector with a longitudinally extending central orifice (preferably smaller in diameter than the skin penetrating devices it is to encase) for receiving drains, intravenous lines and similar skin penetrating devices. FIG. 21 shows an aseptic protector 20 similar to the aseptic protector of FIG. 16–17, but with the skirt 32 secured to the end of the aseptic protector rather than the exterior side surface. FIG. 22 shows an aseptic protector 20 of the present invention which has a truncated cone shape.

In describing the invention, certain embodiments have been used to illustrate the invention and the practices thereof. However, the invention is not limited to these specific embodiments as other embodiments and modifications within the spirit of the invention will readily occur to those skilled in the art on reading this specification. Thus, the invention is not intended to be limited to the specific embodiments disclosed, but is to be limited only by the claims appended hereto.

What is claimed is:

1. An aseptic protector for skin penetrating devices, comprising:

a generally cylindrically shaped body of deformable material; the body of deformable material having a longitudinal centerline, a length parallel to the longitudinal centerline adapted to be greater than a protruding portion of a skin penetrating device to be protected by the body of deformable material and transverse dimensions perpendicular to the longitudinal centerline greater than corresponding transverse dimensions of a skin penetrating device to be protected by the body of deformable material; the body of deformable material having a substantially circular solid cross section except for a slit that extends longitudinally alone the body of deformable material from a first end of the body of deformable material to be placed in contact with a skin surface and from an outer side surface of the body of deformable material to a central portion of the body of deformable material whereby the body of deformable material can be spread apart along the slit to accept and closed for encapsulating a protruding portion of a skin penetrating device to be protected by the body of deformable material from a location where the skin penetrating device protrudes from a skin surface to a location spaced outwardly from the skin surface to buffer and inhibit movement of the skin penetrating device; whereby a second end of the body of deformable material is adapted to encapsulate a free end of the skin penetrating device;

the body of deformable material including aseptic means at the first end for contacting both the skin surface and a skin penetrating device at the location where the skin penetrating device penetrates the skin surface to prevent, inhibit or arrest infection where the skin penetrating device penetrates the skin surface; and an outer tubular casing, with a longitudinal slit aligned with the longitudinal slit in the body of deformable material, encasing the outer side surface of the body of deformable material.

2. The aseptic protector according to claim 1, wherein:

the body of deformable material is deformable to conform to an exterior surface of the skin penetrating device being protected by the body of deformable material.

3. The aseptic protector according to claim 2, wherein:

the body of deformable material is a body, of deformable plastic material.

4. The aseptic protector according to claim 3, wherein:

the aseptic means is dispersed throughout the body of deformable plastic material.

5. The aseptic protector according to claim 2, wherein:

the body of deformable material is a body of deformable resilient material.

6. The aseptic protector according to claim 5, wherein:

the aseptic means is dispersed throughout the body of deformable resilient material.

7. The aseptic protector according to claim 1, wherein:

the outer tubular casing includes means along the longitudinal slit of the outer tubular casing for securing edges of the longitudinal slit of the outer tubular casing together after a protruding portion of a skin penetrating device has been accepted and encapsulated within the body of deformable material.

8. The aseptic protector according to claim 1, wherein:

a skirt of flexible material extends from the tubular casing beyond the first end of the deformable material to form an aseptic veil, about a skin penetrating device being protected by the aseptic protector, that surrounds the location where the skin penetrating device penetrates the skin surface; and the skirt has a longitudinal slit therein extending from the slit in the outer tubular casing whereby the slit in the skirt can be opened and closed when the slits in the tubular casing and body of deformable material are opened and closed to accept and encapsulate a protruding portion of a skin penetrating device.

9. The aseptic protector according to claim 8, wherein:

the outer tubular casing and the skirt include means along the longitudinal slits of the outer tubular casing and the skirt for securing edges of the longitudinal slit of the outer tubular casing and the skirt together after a protruding portion of a skin penetrating device has been accepted and encapsulated within the body of deformable material.

10. The aseptic protector according to claim 1, wherein:

the outer casing is made of a flexible polymeric material that stiffens the aseptic protector.

11. The aseptic protector according to claim 1, wherein:

the aseptic means is dispersed throughout the body of deformable material.

12. The aseptic protector according to claim 1, wherein:

at an end of the body of deformable material for contacting the skin surface, the body of deformable material is adapted to be between about 0.25 inches and about 2.0 inches greater in transverse dimensions than corresponding transverse dimensions of a skin penetrating device to be protected.

13. An aseptic protector for skin penetrating devices, comprising:

an outer, air permeable tubular casing encasing an outer side surface of a solid, generally cylindrically shaped body of material, curable by air, to form a solid, generally cylindrically shaped body of deformable material; means for keeping the body of air curable material from being exposed to air prior to application of the aseptic protector to a skin penetrating device; and the body of deformable material formed by curing the body of air curable material having a longitudinal centerline, a length parallel to the longitudinal centerline greater than a protruding portion of a skin penetrating device to be protected by the body of deformable material and transverse dimensions perpendicular to the longitudinal centerline greater than corresponding transverse dimensions of a skin penetrating device to be protected by the body of deformable material whereby the body of deformable material encapsulates a protruding portion of the skin penetrating device within the body of deformable material from a location where the skin penetrating device protrudes from a skin surface to a location spaced outwardly from the skin surface to buffer and inhibit movement of the skin penetrating device; and the body of deformable material including aseptic means for contacting the skin surface and the skin penetrating device at the location where the skin penetrating device penetrates the skin surface to prevent, inhibit or arrest infection where the skin penetrating device penetrates the skin surface.

14. An aseptic protector for skin penetrating devices, comprising:

a generally cylindrically shaped body of deformable material; the body of deformable material having a first end, to be placed against and conform to a skin surface, which includes aseptic means for contacting both the skin surface and a skin penetrating device at the location where the skin penetrating device penetrates the skin surface to prevent, inhibit or arrest infection where the skin penetrating device penetrates the skin surface;

the body of deformable material having a longitudinal centerline, a length parallel to the longitudinal centerline, and transverse dimensions perpendicular to the longitudinal centerline adopted to be greater than corresponding transverse dimensions of a skin penetrating device to be protected by the body of deformable material; the body of deformable material having means for accepting and encapsulating a protruding portion of a skin penetrating device to be protected by the body of deformable material from a location where the skin penetrating device protrudes from a skin surface to a location spaced outwardly from the skin surface to buffer and inhibit movement of the skin penetrating device; the means for accepting and encapsulating a protruding portion of a skin penetrating device to be protected by the body of deformable material being a longitudinally extending slit in the body of deformable material that extends from an outer side surface of the body of deformable material to a central portion of the body of deformable material adjacent the longitudinal centerline of the body of deformable material whereby the body of deformable material can be spread apart along the slit to accept the protruding portion of the skin penetrating device and closed to encapsulate the protruding portion of the skin penetrating device within the body of deformable material; and an outer tubular casing, with a longitudinal slit aligned with the longitudinal slit in the body of deformable material, encasing the outer side surface of the body of deformable material; the outer tubular casing including a skirt which extends beyond the first end of the deformable material forming an aseptic veil, for placement about a skin penetrating device to be protected by the aseptic protector, that surrounds the location where the skin penetrating device penetrates the skin surface; and the longitudinal slit in the outer tubular casing continuing on into the skirt whereby the slit in the outer tubular casing including the skirt can be opened and closed when the slit in the body of deformable material is opened and closed to accept and encapsulate a protruding portion of a skin penetrating device within the body of deformable material.

15. The aseptic protector according to claim 14, wherein:

the outer tubular casing including the skirt includes means along the longitudinal slit for securing edges of the longitudinal slit together after a protruding portion of a skin penetrating device has been accepted and encapsulated within the body of deformable material.

16. The aseptic protector according to claim 14, wherein:

the body of deformable material has a longitudinally extending central orifice therein.

* * * * *